United States Patent
Homra et al.

(10) Patent No.: US 7,040,484 B1
(45) Date of Patent: May 9, 2006

(54) PROTECTOR FOR ANESTHESIA INSTRUMENTS AND/OR MACHINE

(75) Inventors: Ronald A. Homra, Jackson, TN (US); Theodore E. Nelson, Jackson, TN (US); Ernest E. Wilson, Jackson, TN (US)

(73) Assignee: Mar-Lin Medical, LLC, Jackson, TN (US)

( * ) Notice: Subject to any disclaimer, the term of this patent is extended or adjusted under 35 U.S.C. 154(b) by 397 days.

(21) Appl. No.: 10/391,234

(22) Filed: Mar. 18, 2003

(51) Int. Cl.
*B65D 83/10* (2006.01)

(52) U.S. Cl. .................................................. 206/363

(58) Field of Classification Search ............... 206/38, 206/363, 364, 365, 366, 370, 438, 570, 571, 206/572; 383/38, 39
See application file for complete search history.

(56) References Cited

U.S. PATENT DOCUMENTS

| | | | | |
|---|---|---|---|---|
| 4,476,860 A | * | 10/1984 | Collins et al. ............. | 128/853 |
| 5,133,097 A | * | 7/1992 | Pyles ........................... | 5/623 |
| 5,135,144 A | * | 8/1992 | Blakely et al. ............. | 224/240 |
| 5,170,804 A | * | 12/1992 | Glassman .................... | 128/849 |
| 5,396,672 A | * | 3/1995 | Brown ......................... | 5/600 |
| 5,423,450 A | * | 6/1995 | Shillington et al. ......... | 220/481 |
| 5,511,674 A | * | 4/1996 | Boyd et al. ................. | 211/70.6 |
| 5,533,618 A | * | 7/1996 | Pickels, Jr. ................. | 206/363 |
| 6,142,152 A | * | 11/2000 | Gawarecki .................. | 128/849 |
| 6,691,868 B1 | * | 2/2004 | Roshdy ....................... | 206/366 |
| 6,905,022 B1 | * | 6/2005 | Horrell ........................ | 206/438 |
| 6,913,150 B1 | * | 7/2005 | Fountain ..................... | 206/570 |
| 6,918,488 B1 | * | 7/2005 | Renhed ....................... | 206/440 |

* cited by examiner

*Primary Examiner*—Kurt Fernstrom
(74) *Attorney, Agent, or Firm*—Walker, McKenzie & Walker, P.C,.

(57) ABSTRACT

A protector for use with an anesthesia machine and anesthesia instruments. The protector includes a container member having a cavity for holding an anesthesia instrument and having an open mouth for allowing ingress and egress into the cavity; and securing structure for securing the container member to the anesthesia machine.

2 Claims, 4 Drawing Sheets

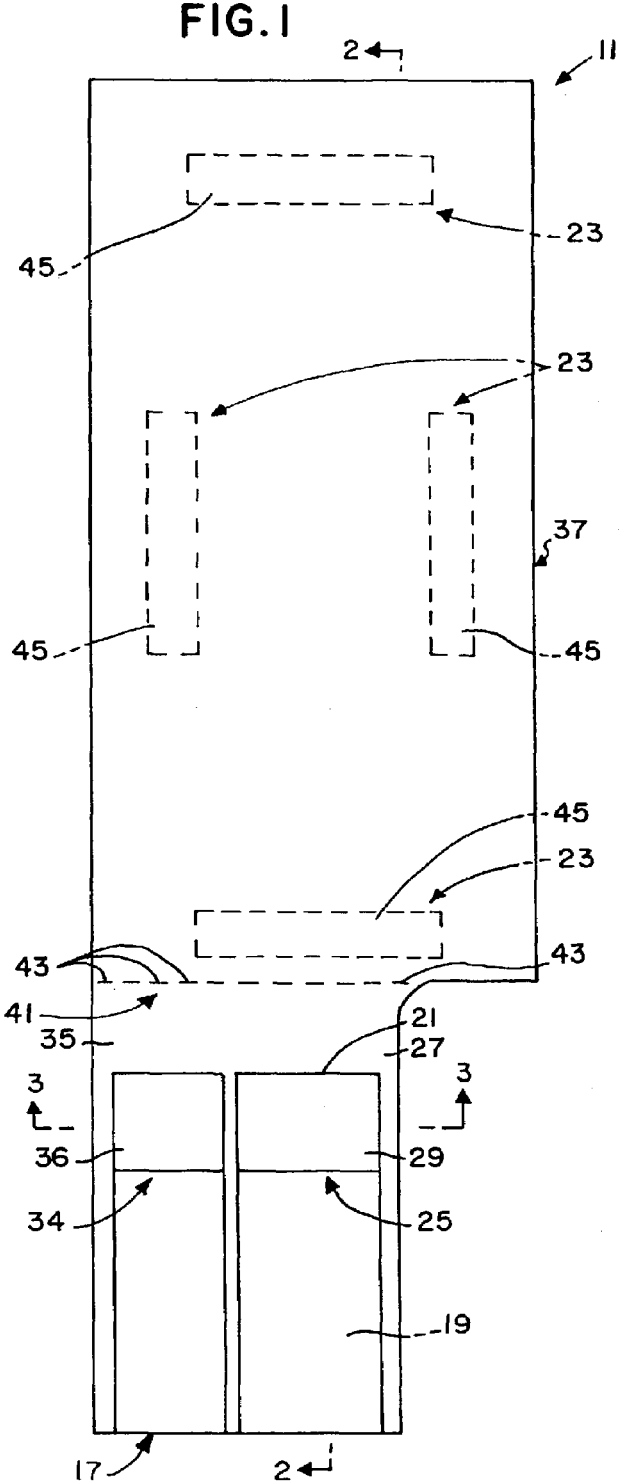
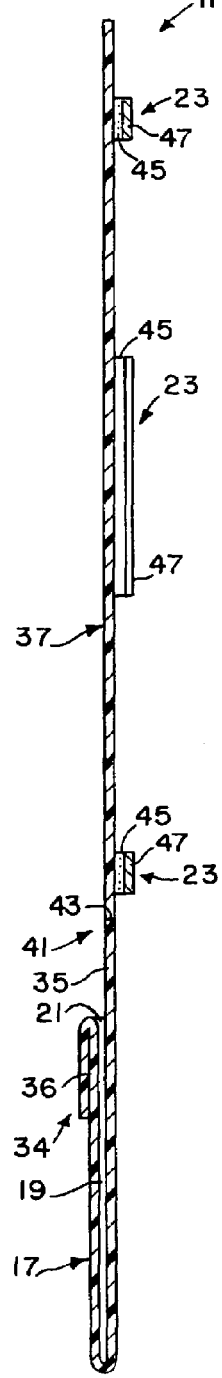

PROTECTOR FOR ANESTHESIA INSTRUMENTS AND/OR MACHINE

BACKGROUND OF THE INVENTION

1. Field of the Invention

The present invention relates, in general, to means for helping to maintain a clean or sterile operating field during medical procedures, and in particular, to a protector for enclosing one or more anesthesia instruments after initial use and/or for covering at least a portion of the work or tabletop surface of an anesthesia machine, etc.

2. Information Disclosure Statement

During medical procedures in which general anesthesia is used, the anesthesiologist typically uses an "anesthesia machine" to facilitate, control and monitor the anesthesia process. "Anesthesia machine" is defined herein to include both a simple cart which may consist simply of a small cabinet or table, typically on wheels, that the anesthesiologist can use to contain and/or support various "anesthesia instruments" such as laryngeal mask airways ("LMA") and the like, and an apparatus which may consist of the combination of such a cart and various means used by the anesthesiologist during general anesthesia and the like for controlling and monitoring the vital functions of an anesthetized patient. Such means may include controls for the flow and mixtures of oxygen and a gaseous anesthetic to the patient; gauges or indicators for monitoring the flow rates and supply pressures; spirometers that measure respiratory volumes within the breathing circuit; ventilators; waste gas scavengers; means for monitoring patient temperature, blood pressure, pulse rate, oxygen and carbon dioxide concentrations and electrocardiographic data; computers to facilitate monitoring of variables such as blood pressure, heart rate, etc.

Nothing in the known prior art, either singly or in combination, discloses or suggests the present invention.

BRIEF SUMMARY OF THE INVENTION

The present invention is designed for use by an anesthesiologist during an operation. More specifically, the present invention provides a sterile protector for attachment to an anesthesia machine on which the anesthesiologist can place various anesthesia instruments such as laryngoscope, laryngeal mask airways, etc., during the operation, and into which the anesthesiologist can insert non-sterile instruments for safe transfer to sterilization chambers, etc.

The protector of the present invention includes, in general, a container member having a cavity for holding an anesthesia instrument and having an open mouth for allowing ingress and egress into the cavity; and securing structure for securing the container member to an anesthesia machine.

BRIEF DESCRIPTION OF THE SEVERAL VIEWS OF THE DRAWINGS

FIG. 1 is a top plan view of the protector of the present invention.

FIG. 2 is a sectional view of the protector of the present invention substantially as taken on line 2—2 of FIG. 1 with certain features enlarged to more clearly show the invention.

FIG. 3 is a sectional view of the protector of the present invention substantially as taken on line 3—3 of FIG. 1 on a somewhat enlarged scale and with certain features omitted to more clearly show the invention.

DETAILED DESCRIPTION OF THE INVENTION

Figure 4:
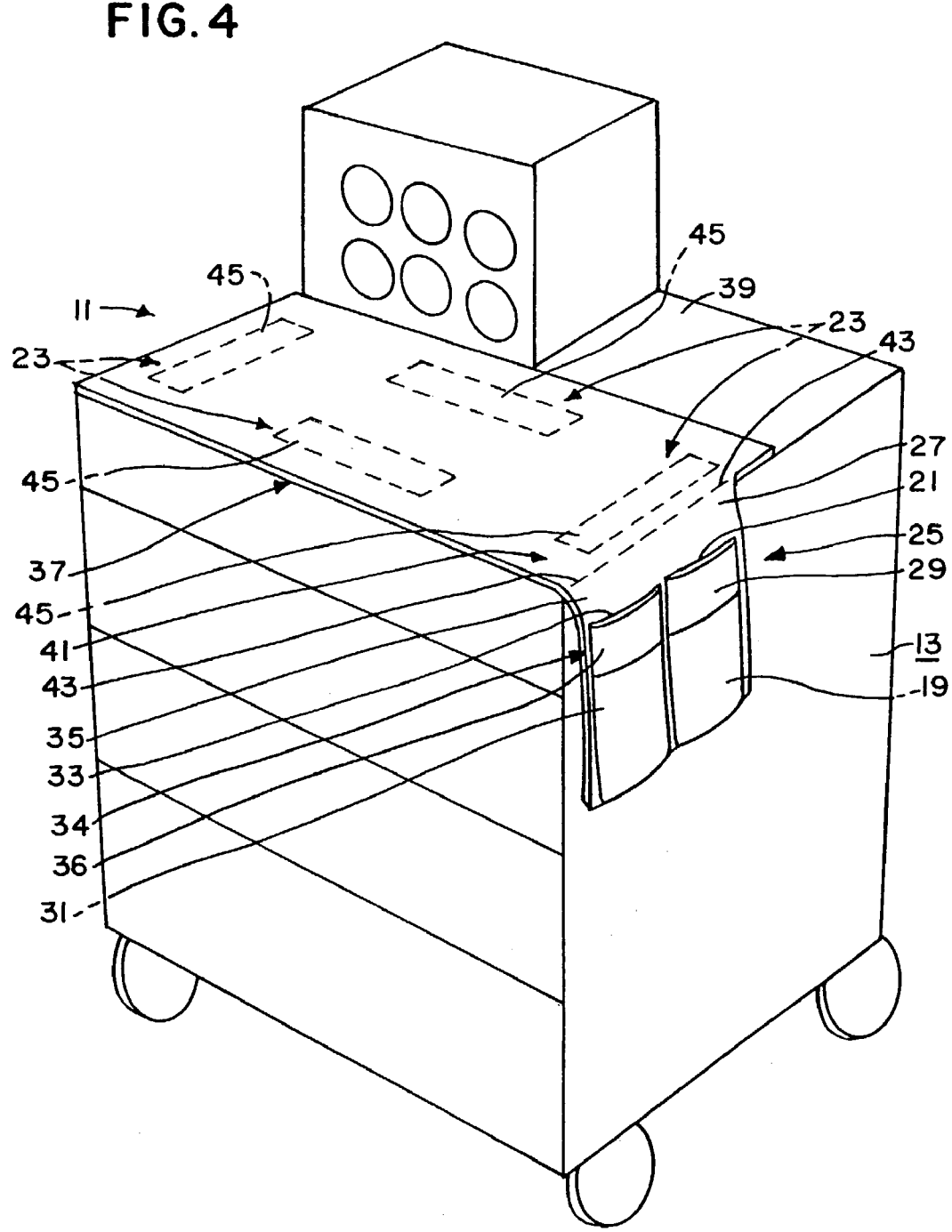
FIG. 4 is a perspective view of the protector of the present invention, shown in combination with an anesthesia machine.
Figure 5:
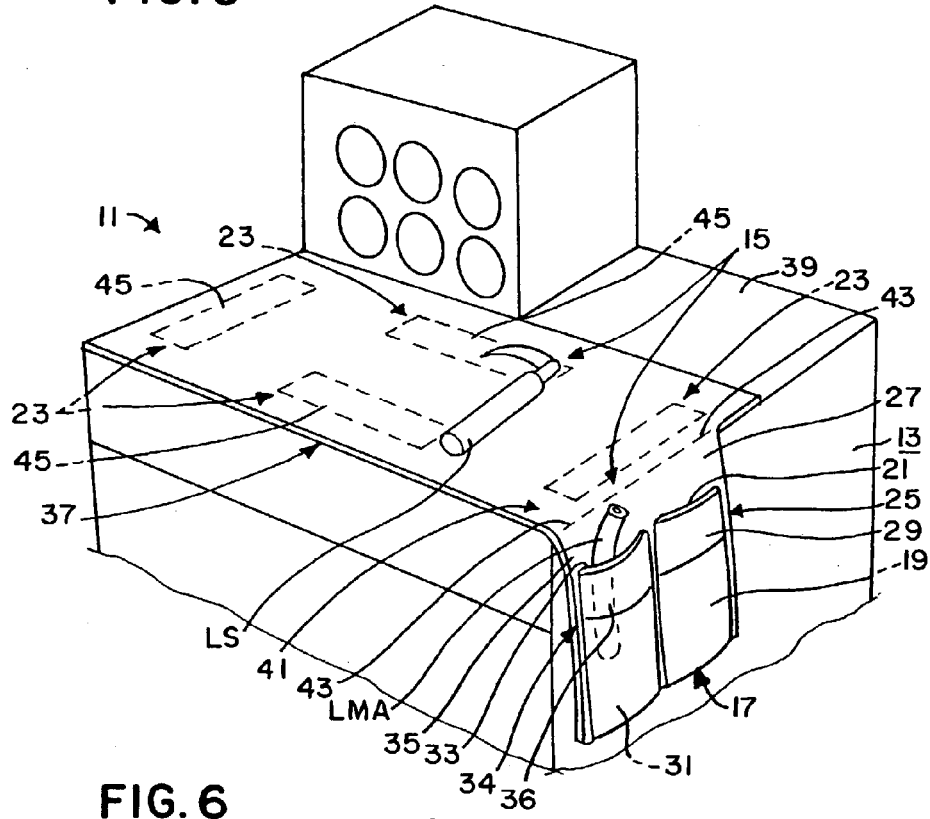
FIG. 5 is a perspective view similar to FIG. 4 but showing various anesthesia instruments in combination therewith and with portions of the anesthesia machine broken away.
Figure 6:
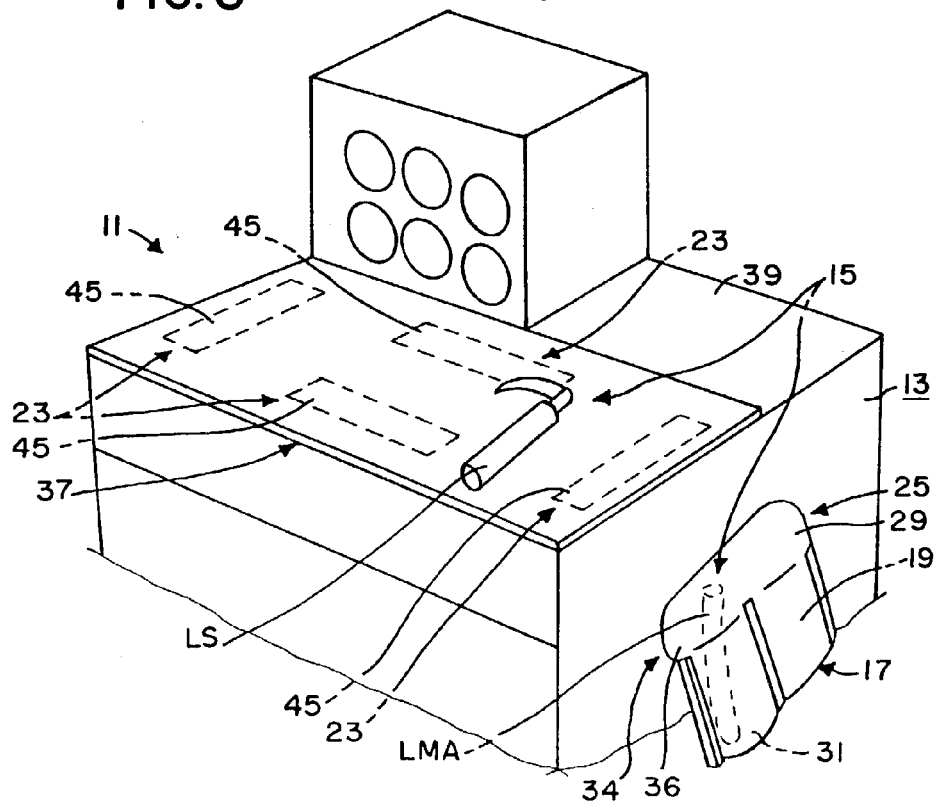
FIG. 6 is a perspective view similar to FIG. 5 but showing one anesthesia instrument positioned within a container member of the protector of the present invention, with the container member torn away from a cover member of the protector of the present invention and closed over the anesthesia instrument.
Figure 7:
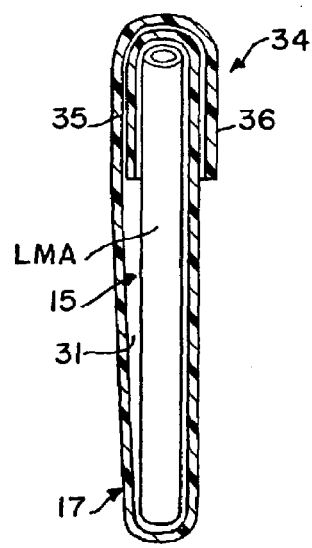
FIG. 7 is a somewhat diagrammatic sectional view substantially as taken on line 7—7 of FIG. 6.
Figure 8:
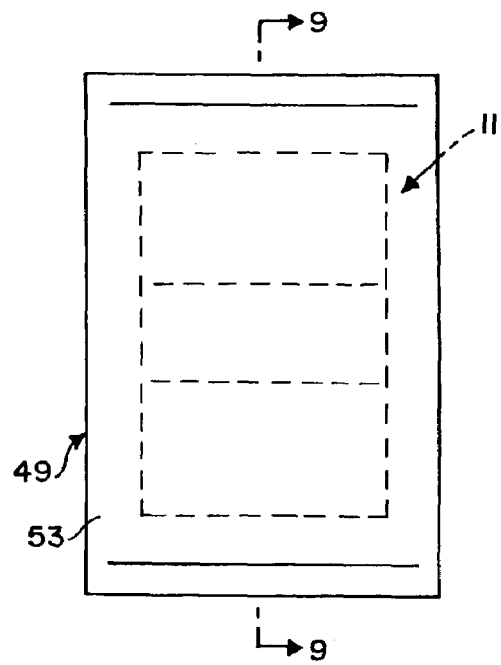
FIG. 8 is a plan view of a sterile envelope containing the protector of the present invention.
Figure 9:
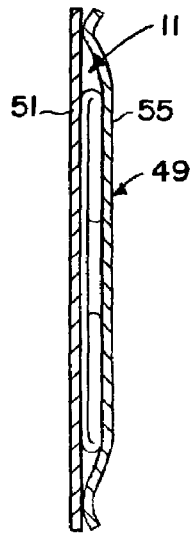
FIG. 9 is a sectional view substantially as taken on line 9—9 of FIG. 8.

A preferred embodiment of the protector of the present invention is shown in FIGS. 1–11, and identified by the numeral 11. The protector 11 is designed for use with an anesthesia machine 13, and various anesthesia instruments 15 such as a laryngoscope LS and/or a laryngeal mask airway LMA, etc. As hereinabove explained in more detail, "anesthesia machine" is defined herein to include both a simple cart which may consist simply of a small cabinet or table, typically on wheels, that the anesthesiologist can use to contain and/or support various anesthesia instruments 15, etc., and an apparatus which may consist of the combination of such a cart and various means used by the anesthesiologist during general anesthesia and the like for controlling and monitoring the vital functions of an anesthetized patient.

The protector 11 includes a container member 17 having a cavity 19 for holding an anesthesia instrument 15 and having an open mouth 21 for allowing ingress and egress into the cavity 19; and includes securing means 23 for securing the container member 17 to the anesthesia machine 15.

The container member 17 may include closure means 25 for closing the open mouth 21 thereof. The closure means 25 may be of various specific types such as a typical slide fastener or zipper-type plastic bag closure, etc. For simplicity of use and manufacture, the closure means 25 may include a common fold-lock plastic "sandwich bag" construction in which the open mouth of a bag has a flap provided on the one lip for being tucked into the mouth and a cuff provided on the other lip for being folded over the flap, etc., to close the opening. Thus, the closure means 25 may include an elongated flap or tab 27 and a cuff 29.

The container member 17 may have a second cavity 31 for holding an anesthesia instrument 15 or the like, a second open mouth 33 for allowing ingress and egress into the second cavity 31, and second closure means 34 for closing the second open mouth 33 thereof. The second closure means 34 may be identical in construction and operation to the closure means 25, and may include an elongated flap or tab 35 and a cuff 36.

The protector 11 preferably includes a cover member or drape 37 for covering at least a portion of the anesthesia machine 13. Thus, the anesthesia machine 13 typically includes a substantially horizontal work surface 39 on which the anesthetist commonly places anesthesia instruments 15 such as a laryngoscope LS and the like during general anesthesia, etc., and the cover member 37 is preferably designed as a substantially flat sheet for lying or draping over all or a portion of the work surface 39 to provide a sterile field for the anesthetist to place anesthesia instruments or the like.

Figure 10:
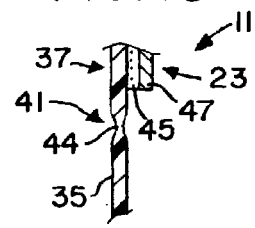
FIG. 10 is a sectional view of a portion of the protector of the present invention, showing an alternate embodiment of the separation means thereof.

The container member 17 is preferably attached to the cover member 37, and the protector 11 preferably includes separation means 41 for allowing separation of the container member 17 from the cover member 37 when desired. The separation means 41 may include a line of spaced apart perforations 43 between the container member 17 and the cover member 37 for allowing the container member 17 to be easily torn from the cover member 37 as will now be apparent to those skilled in the art. An alternate embodiment of the separation means 41 is shown in FIG. 10 in which the separation means 41 consist of an area or strip 44 of relative thin material between the container member 17 and the cover member 37 for allowing the container member 17 to be easily torn from the cover member 37 as will now be apparent to those skilled in the art.

The securing means 23 is preferably designed for securing the cover member 37 to the work surface 39 of the anesthesia machine 15, and, since the container member 17 is attached to the cover member 37 until torn therefrom, indirectly secure the container member 17 to the work surface 39 of the anesthesia machine 15. The securing means 23 preferably includes adhesive means, e.g., a plurality of strips 45 of double sided adhesive tape, for securing the cover member 37 to the anesthesia machine 15. One side of each strip 45 of adhesive tape is preferably stuck to the back side of the cover member 37 at strategic locations as shown in FIGS. 1 and 4–6. A removable backing member 47 is preferably provided on other side of each strip 45 of adhesive tape to prevent that side from being inadvertently stuck to something until the backing member 47 is intentionally removed to allow the cover member 17, and container member 17, to be secured or stuck to the work surface 39 of the anesthesia machine 13. The securing means 23 could, alternatively, merely consist of some type of sticky coating on the back side of the cover member 17 as will now be apparent to those skilled in the art.

Figure 11:
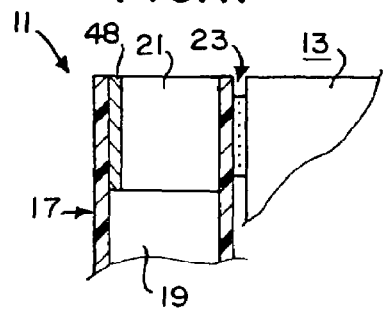
FIG. 11 is a somewhat diagrammatic sectional view of a portion of the protector of the present invention showing certain alternate features thereof.

The protector 11 can be manufactured in various manners, out of various materials, and in various shapes and sizes as will now be apparent to those skilled in the art. For example, the container member 17 and cover member 37 of the protector 11 may be formed of a relative thin thermoplastic material sheet that is generally impermeable to viral and bacterial contamination, cut into the desired shape and size with the cavities 19, 31 and cuff-type closure means 25, 34 of the container member 17 folded and heat sealed or welded, etc., as will now be apparent to those skilled in the art. The line of spaced apart perforations 43 (i.e., the separation means 41) can be cut or otherwise formed in the sheet at the junction between the container member 17 and cover member 37. The strips 23 of adhesive tape (i.e., the securing means 23) can be merely stuck to the bottom side of the sheet in the desired locations. A portion of the protector 11 (i.e., the container member 17) is shown in FIG. 11 with a memory or formable strip 48 included to normally hold the open mouth 21 slightly gaped open for allowing easy insertion of an anesthesia instruments or the like into the cavity 19. FIG. 11 shows the protector 11 merely as a pouch-like member (i.e., the container member 17 without the cover member 37), and shows the securing means 23 securing the top of the container member 17 to the anesthesia machine 15.

The protector 11 may be packaged in a sterile envelope or package 49 (see FIGS. 8 and 9) so that the protector 11 can be maintained clean and sterile prior to use. The sterile envelope 49 may be of various constructions and designs now apparent to those skilled in the art. For example, the envelope 49 may include back panel 51 make of a plastic sheet or the like on which the protector 11 can be folded and placed on, and a front panel 53 made of a plastic sheet or the like for covering the folded protector 11 and the back panel 51 with the edges of the front panel 53 heat sealed or welded to the back panel 51 in a manner which allows the front panel 53 to be quickly separated from the back panel 51 so that the protector 11 can be removed therefrom.

To use the protector 11 to protect the work surface 39 of an anesthesia machine 13 and/or to contain one or more contaminated anesthesia instruments 15, the protector 11 is merely secured to the anesthesia machine 13 in the desired location, e.g., with the cover member 37 draping over or covering all or a portion of the work surface 39 and/or with the container member 17 hanging down from the edge of the work surface 39. The anesthesiologist can then safely place contaminated anesthesia instruments 15 (e.g., an laryngoscope LS) on the cover member 37 and/or safely insert contaminated anesthesia instruments 15 (e.g., an laryngeal mask airway LMA) into one or both cavities 19, 31. When desired to transfer the contaminated anesthesia instruments 15 (e.g., an laryngeal mask airway LMA) held in the container member 17 from the anesthesia machine 13 to a sterilization chambers, disposal structure, etc., the container member 17 can be merely torn from the cover member 37 or otherwise removed from the anesthesia machine 13, and one or both closure means 25, 34 folded over the associated cavity 19, 31 or otherwise used to close the associated mouth 21, 33 to seal the contaminated anesthesia instruments 15 within the cavity 19, 31, thus allowing the contaminated anesthesia instruments 15 to be safely transferred to a sterilization chambers, disposal structure, etc. The cover member 37 can merely be pulled from the work surface 39 and disposed of in a safe disposal structure, etc.

Although the present invention has been described and illustrated with respect to a preferred embodiment and a preferred use therefor, it is not to be so limited since modifications and changes can be made therein which are within the full intended scope of the invention.

The invention claimed is:

1. A protector for use with an anesthesia machine and anesthesia instruments; said protector comprising:
   (a) a cover member for covering at least a portion of an anesthesia machine:
   (b) a container member attached to said cover member, said container member having a cavity for holding an anesthesia instrument and having an open mouth for allowing ingress and egress into said cavity;
   (c) securing means for securing said container member to an anesthesia machine; and
   (d) separation means for allowing separation of said container member from said cover member.

2. The protector of claim 1, in which said separation means includes a line of spaced apart perforations between said container member and said cover member for allowing said container member to be torn from said cover member.

* * * * *